United States Patent
Rowe

(10) Patent No.: US 10,926,002 B2
(45) Date of Patent: Feb. 23, 2021

(54) METAL MATRIX COMPOSITE ORTHOPEDIC REPLACEMENTS

(71) Applicant: Toyota Motor Engineering & Manufacturing North America, Inc., Plano, TX (US)

(72) Inventor: Michael Paul Rowe, Pinckney, MI (US)

(73) Assignee: Toyota Motor Engineering & Manufacturing North America, Inc., Plano, TX (US)

(*) Notice: Subject to any disclaimer, the term of this patent is extended or adjusted under 35 U.S.C. 154(b) by 49 days.

(21) Appl. No.: 16/230,184

(22) Filed: Dec. 21, 2018

(65) Prior Publication Data

US 2020/0197573 A1 Jun. 25, 2020

(51) Int. Cl.

| | |
|---|---|
| *A61F 2/28* | (2006.01) |
| *A61L 27/42* | (2006.01) |
| *A61L 27/08* | (2006.01) |
| *A61L 27/04* | (2006.01) |
| *A61L 27/10* | (2006.01) |

(52) U.S. Cl.
CPC .......... *A61L 27/422* (2013.01); *A61L 27/047* (2013.01); *A61L 27/08* (2013.01); *A61L 27/427* (2013.01); *A61F 2310/00185* (2013.01); *A61F 2310/00269* (2013.01); *A61L 27/10* (2013.01)

(58) Field of Classification Search
CPC ........ A61F 2/30965; A61F 2002/30971; A61F 2/28; A61B 2017/00964; A61L 27/422; A71L 27/427
See application file for complete search history.

(56) References Cited

U.S. PATENT DOCUMENTS

| | | | |
|---|---|---|---|
| 7,270,679 B2 | 9/2007 | Istephanous et al. | |
| 8,052,745 B2* | 11/2011 | Weber | A61F 2/90 623/1.15 |
| 8,168,291 B2* | 5/2012 | Shah | C04B 35/803 428/293.4 |
| 9,435,014 B2* | 9/2016 | Rohatgi | C22C 49/14 |
| 2004/0005462 A1 | 1/2004 | Fukagawa et al. | |
| 2004/0243241 A1 | 12/2004 | Istephanous et al. | |
| 2011/0033721 A1* | 2/2011 | Rohatgi | B22D 19/14 428/548 |

(Continued)

OTHER PUBLICATIONS

Shirvanimoghaddam et al., "Carbon fiber reinforced metal matrix composites: Fabrication process and properties," Composites: Part A, 92, 70-96 (2017).

(Continued)

*Primary Examiner* — Jason-Dennis N Stewart
(74) *Attorney, Agent, or Firm* — Christopher G. Darrow; Darrow Mustafa PC

(57) ABSTRACT

Orthopedic replacements include are formed at least partially of composite materials including a metal matrix with reinforcing carbon fiber integrated into the matrix. The composite materials have substantially lower density than metal, and are expected to have appreciable strength. The orthopedic replacements can include a bone attachment portion and a load bearing portion. In some versions, the orthopedic replacements can include a core formed of the composite material, with a shape completion portion, formed for example from plastic, at least partially coating the core.

14 Claims, 5 Drawing Sheets

(56) References Cited

U.S. PATENT DOCUMENTS

| | | | |
|---|---|---|---|
| 2011/0124483 A1* | 5/2011 | Shah | C04B 20/12 |
| | | | 501/32 |
| 2012/0153216 A1 | 6/2012 | Wrosch | |
| 2013/0340896 A1* | 12/2013 | Rohatgi | B22D 19/02 |
| | | | 148/402 |
| 2015/0375478 A1* | 12/2015 | Gruhn | B32B 7/12 |
| | | | 442/286 |
| 2018/0079884 A1 | 3/2018 | Rowe | |
| 2019/0168420 A1 | 6/2019 | Reese et al. | |

OTHER PUBLICATIONS

Adebisi et al., "Metal Matrix Composite Brake Rotors: Historical Development and Product Life Cycle Analysis," International Journal of Automotive and Mechanical Engineering (IJAME), vol. 4, pp. 471-480, (2011).

Miracle, D.B., "Metal matrix composites—From science to technological significance," Composites Science and Technology, 65, pp. 2526-2540 (2005).

Ceschini, L. et al., Aluminum and Magnesium Metal Matrix Nanocomposites, Springer Nature Singapore Pte Ltd., ISBN 978-981-10-2681-2 (eBook) (2017).

Embury, D. et al., "Steel-Based Composites: Driving Forces and Classifications," Annu. Rev. Mater. Res., 40:213-41 (2010).

Mortensen, A. et al., "Metal Matrix Composites," Annu. Rev. Mater. Res., 40:243-70 (2010).

\* cited by examiner

METAL MATRIX COMPOSITE ORTHOPEDIC REPLACEMENTS

TECHNICAL FIELD

The present disclosure generally relates to orthopedic replacements and, more particularly, to orthopedic replacements formed from metal/carbon fiber composite materials.

BACKGROUND

The background description provided herein is for the purpose of generally presenting the context of the disclosure. Work of the presently named inventors, to the extent it may be described in this background section, as well as aspects of the description that may not otherwise qualify as prior art at the time of filing, are neither expressly nor impliedly admitted as prior art against the present technology.

Damaged bones and joints can be replaced with a prosthetic, or orthopedic replacement, such as an artificial hip. Such orthopedic replacements are often formed of metal, a plastic, or a composite material having a plastic matrix integrated with a reinforcing fiber. Carbon fiber is a commonly used reinforcing fiber, due to its unusually high strength-to-weight ratio.

Metal matrix composite materials having a matrix formed of metal, incorporated with reinforcing fibers, are known and can have high strength-to-weight ratios. Conventional methods for forming such materials typically involves solidifying molten metal matrix around the fibers, or sintering metal matrix powder around the fibers. Such methods generally require that the thermal decomposition temperature of the fiber material be higher than the melting temperature or the sintering temperature of the metal matrix material; otherwise the reinforcing fibers will be destroyed during manufacture. Because of this requirement, and the fact that the melting temperature or sintering temperature of the strongest metal are high (e.g. melting temperature >1500° C. for titanium, sintering temperature >1100° C. for stainless steel powder), only structural fibers having considerably high thermal decomposition temperatures, such as ceramic fibers, can be used.

It would be desirable to form orthopedic replacement parts from metal matrix composites reinforced with carbon fiber in order to enhance the strength-to-weight ratio of the composite, and to provide methods capable of forming such composite orthopedic replacements.

SUMMARY

This section provides a general summary of the disclosure, and is not a comprehensive disclosure of its full scope or all of its features.

In various aspects, the present teachings provide an orthopedic replacement having a bone connection portion and a load bearing portion. The load bearing portion has a continuous metal matrix of sintered metal nanoparticles and at least one reinforcing carbon fiber that is at least partially encapsulated within the metal matrix. In some implementations, the at least one reinforcing carbon fiber is fully encapsulated within the continuous metal matrix. In some implementations, the composite material can have density less than 5 g/cm³.

In other aspects, the present teachings provide an orthopedic replacement having a structural core and a shape completion material at least partially covering the structural core. The structural core is formed of a composite material that includes at least one reinforcing carbon fiber, and a continuous metal matrix, of sintered metal nanoparticles, disposed around the at least one reinforcing carbon fiber.

In still other aspects, the present teachings provide a method for forming an orthopedic replacment. The method includes a step of providing metal nanoparticles and a step of combining metal nanoparticles with a reinforcing carbon fiber component to form an unannealed combination. The method further includes a step of sintering the metal nanoparticles around the reinforcing carbon fiber component by applying elevated temperature to the unannealed combination.

Further areas of applicability and various methods of enhancing the above coupling technology will become apparent from the description provided herein. The description and specific examples in this summary are intended for purposes of illustration only and are not intended to limit the scope of the present disclosure.

BRIEF DESCRIPTION OF THE DRAWINGS

The present teachings will become more fully understood from the detailed description and the accompanying drawings, wherein.

It should be noted that the figures set forth herein are intended to exemplify the general characteristics of the methods, algorithms, and devices among those of the present technology, for the purpose of the description of certain aspects. These figures may not precisely reflect the characteristics of any given aspect, and are not necessarily intended to define or limit specific embodiments within the scope of this technology. Further, certain aspects may incorporate features from a combination of figures.

DETAILED DESCRIPTION

The present disclosure generally relates to orthopedic replacements formed from carbon fiber metal matrix composites (CF-MMCs). The CF-MMCs have a continuous metal matrix, with a reinforcing carbon fiber integrated into the matrix. The CF-MMCs have a substantially lower density than the pure metal, and have appreciable strength.

CF-MMCs used to form orthopedic replacements of the present teachings can have a metal matrix formed from a high strength metal, such as steel, titanium, or various alloys or carbides. Disclosed methods for forming a CF-MMC involve sintering metal nanoparticles around carbon fiber to form a continuous matrix. The use of nanoparticles lowers the sintering temperature to less than the thermal degradation temperature of carbon fiber (about 450° C.), thereby enabling formation of the fiber reinforced composite. Because nanoparticles of many of the desire metal matrix materials, having sufficiently small size, are not commonly available, the nanoparticles are provided using a proprietary synthetic route. The result of the sintering process is an orthopedic replacement having layer of a reinforcing carbon fiber interpenetrated in the metal matrix, thereby providing increased strength-to-weight ratio. For example, an orthopedic replacement of the present disclosure can have significantly lower density than a pure metal orthopedic replacement, while having considerable structural strength, including tensile strength.

Figure 1:
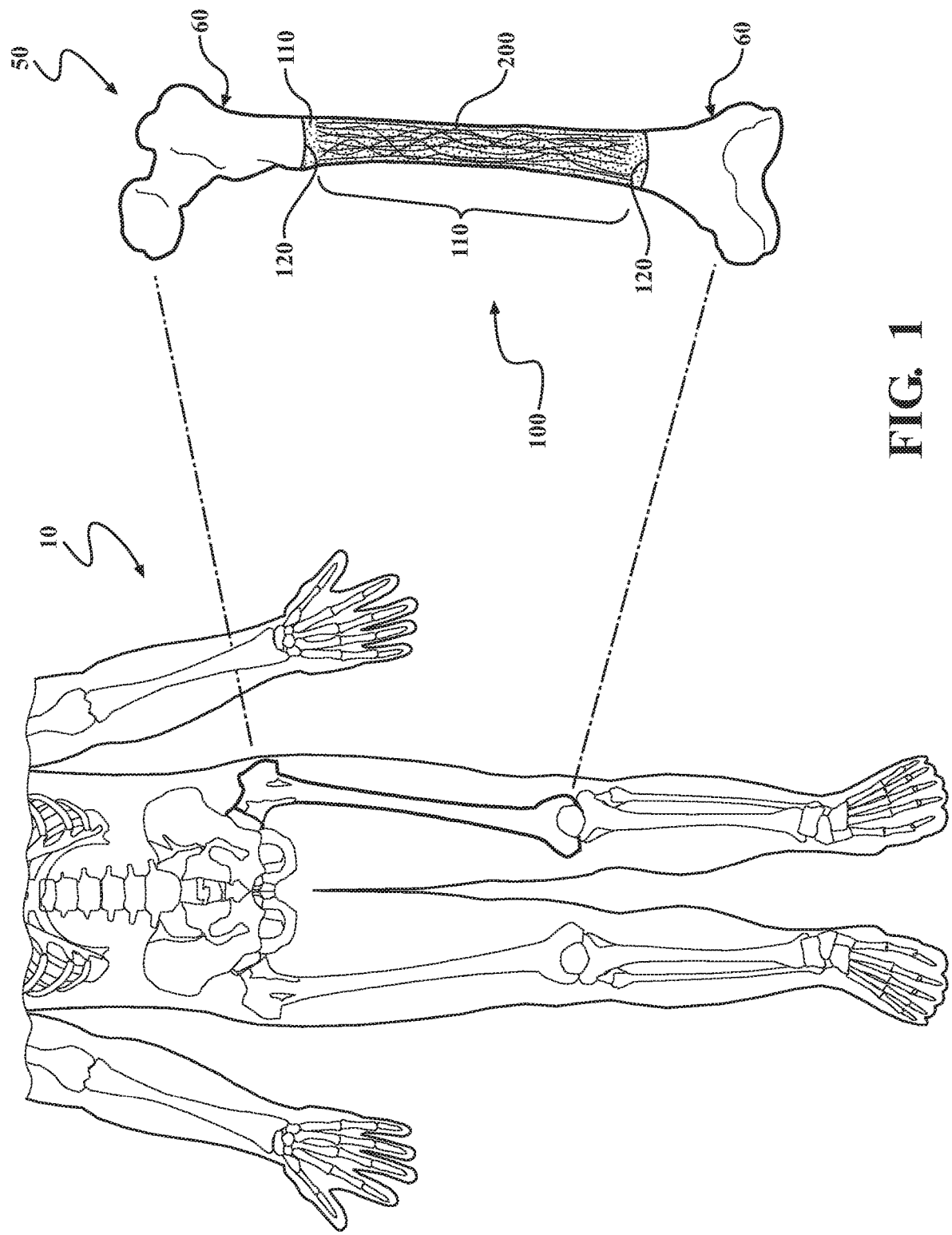
FIG. 1 is a front view of a human body, with a magnified view of a femur bone having an orthopedic replacement of the present teachings.
Figure 2:
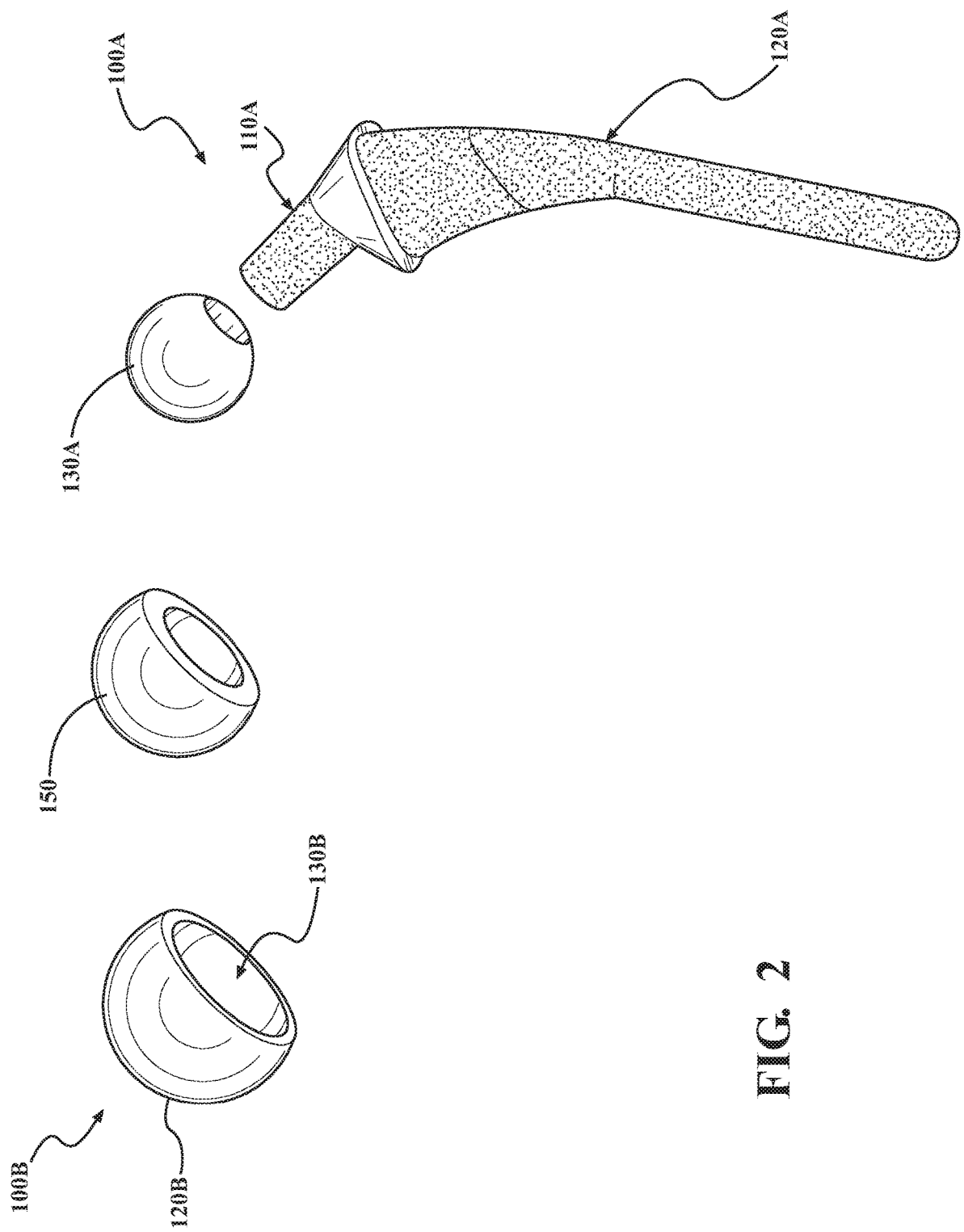
FIG. 2 is a perspective view of an artificial hip constituting an alternative implementation of an orthopedic replacement of the present teachings.

FIGS. 1 and 2 show different exemplary implementations of orthopedic replacements 100 of the present teachings. As used herein, the phrase, "orthopedic replacement" refers to a structure shaped to replace all or a portion of a bone, typically a human bone. For example, an orthopedic replacement 100 of the present teachings can be molded to have the shape of entire femur bone, or a portion of a femur bone, as shown in FIG. 1. FIG. 1 shows a front view of a human body 10, providing a view of the skeleton and emphasizing a femur bone 50. The femur bone 50 of FIG. 1 is a natural/artificial hybrid bone, having natural bone portions 60 and an orthopedic replacement 100 of the present teachings connecting them and replacing a damaged bone portion. The orthopedic replacement 100 of FIG. 1, constituting a portion of a femur bone, includes a load bearing portion 110. The load bearing portion 110 is configured to bear a load at least equal to a normal load born by the replaced bone or bone portion during bodily activity. The load bearing portion 110 will thus generally approximate the shape of the replaced bone, and can, but need not necessarily, mimic the exact dimensions and shape of the replaced bone.

The orthopedic replacement of FIG. 1 additionally has two bone attachment portions 120. The bone attachment portions 120 are portions of the orthopedic replacement that are configured to be attached—via adhesive, pins, or any other suitable means—to natural bone 60, thereby integrating the orthopedic replacement into a complete natural/artificial bone. It will be understand that in some implementations, such as implementations in which an orthopedic replacement 100 is formed to replace an entire bone, the orthopedic replacement 100 may not include a bone attachment portion 120. The orthopedic replacement 100 is composed partly or entirely of carbon fiber metal matrix composite (CF-MMC) 200, as discussed in greater detail below.

In some implementations, an orthopedic replacement 100 of the present teachings can include an artificial joint, such as the artificial hip of FIG. 2. The orthopedic replacement of FIG. 2 includes first and second replacement portions 100A and 100B. The first replacement portion 100A replaces the upper portion of a femur bone, and includes a load bearing portion 110, a bone attachment portion 120, and first joint surface 130A. In this instance the bone attachment portion 120 is a shaft designed to be inserted into a hole drilled into a severed femur bone, and the first joint surface 130A is a smooth ball attached at the top of the load bearing portion 110.

The second replacement portion 100B of FIG. 2 includes a bone attachment portion 110 configured to be attached at the bottom of a pelvic bone, and a second joint surface 130B complementary to the first joint surface 130A, forming a ball-and-socket joint. In many implementations, it will be desirable that at least one load bearing portion 110 and/or at least one bone attachment portion 120 is formed substantially of a CF-MMC 200 of the present teachings. In certain implementations, most or all of a load bearing portion 110 can be formed of a CF-MMC 200. This is because these portions are likely to be the largest and thus confer the greatest benefit when formed of a high strength-to-weight ratio material.

Figure 3A:
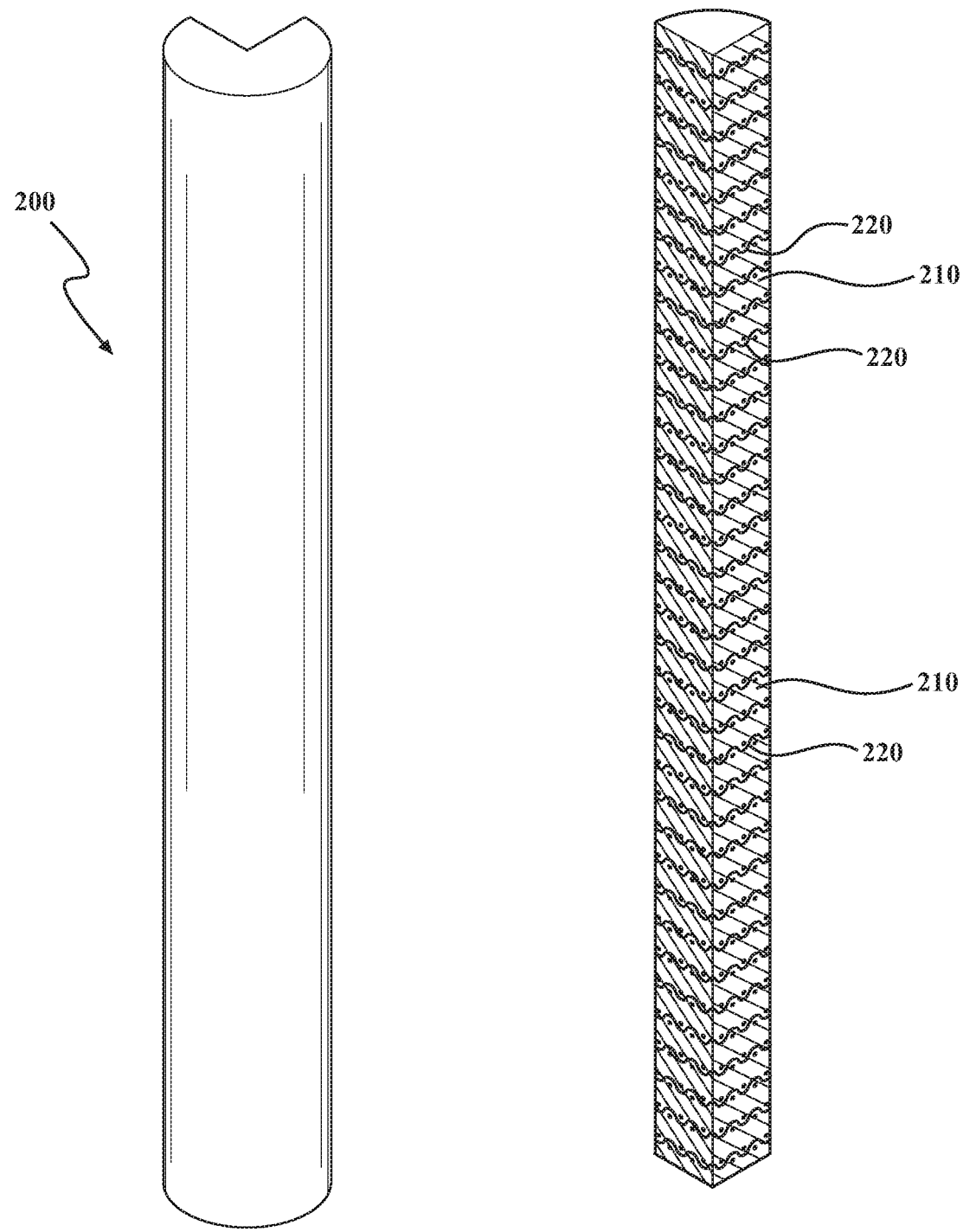
FIG. 3A is a perspective view of a cylinder of carbon fiber metal matrix material such as can be incorporated into an orthopedic replacement of the present teachings, the cylinder including a cutaway portion to facilitate viewing the inside of the material.

FIG. 3A shows a perspective view of a CF-MMC 200 having a simplified cylindrical shape. The simplified shape of FIG. 3A is presented to show the components of the CF-MMC 200. A CF-MMC having such a simplified shape can be utilized as an orthopedic replacement 100, such as a replacement of a portion of bone when anatomically exact shape is not required. In other implementations, discussed in greater detail below, a CF-MMC 200 having a simplified shape such as that shown in FIG. 3A can be used as the core of an orthopedic replacement 100, in combination with other components. The CF-MMC 200 of FIG. 3A, from which all or a portion of an orthopedic replacement 100 is formed, includes a continuous metal matrix 210 and a reinforcing carbon fiber 220 that is at least partially encapsulated within the continuous metal matrix 210. As shown, the reinforcing carbon fiber 220 can be provided as a layer of fabric, cloth, weave, woven yarn, etc. In other instances, the reinforcing carbon fiber 220 can be provided as a fiber, yarn, or a plurality of aligned fibers.

Figure 3B:
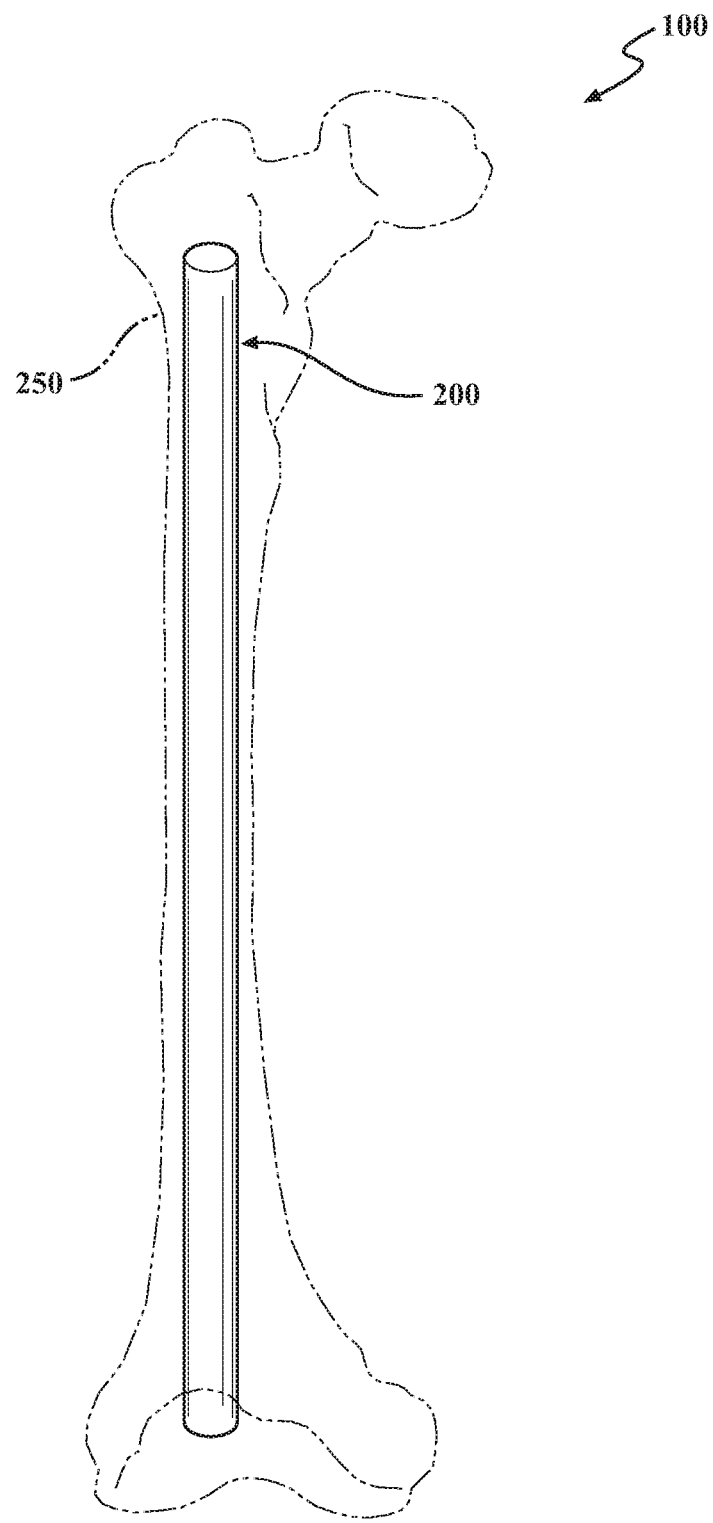
FIG. 3B is a perspective view of a femur is a pictorial view of a portion of a method for forming a composite material of the type shown in FIG. 1.

FIG. 3B shows an implementation in which a CF-MMC 200 form the core of an orthopedic replacement 100. In such implementations, the CF-MMC 200 can the core, such as a load-bearing core, of an orthopedic replacement. Further in such implementations, the CF-MMC 200 can be at least partially covered with a shape completion material 250 that is configured to fill out the shape of the bone that is being replaced. In various implementations, the shape completion material can be composed of any suitable material, such as a plastic or ceramic that is suitable and convenient for manufacturing to adopt the desired shape.

It will be appreciated that implementations in which a CF-MMC 200 forms the core of an orthopedic replacement, and is at least partially covered with a shape completion material 250, can be useful and cost-effective for manufacturing purposes. This is because such implementations facilitate a simplified shape of the CF-MMC 200 that may be easier to manufacture. In addition, the shape completion material 250 can be easily formed around the CF-MMC 200, for example by injection molding of a suitable plastic.

The continuous metal matrix 210 generally includes sintered metal nanoparticles, and compositionally includes at least one metal or metal alloy, such as stainless steel, titanium, or titanium carbide. The continuous metal matrix 210 can optionally include any, several, or all, of: manganese, nickel, chromium, molybdenum, boron, titanium, vanadium, tungsten, cobalt, niobium, phosphorus, sulfur, and silicon. Relative ratios of the various elemental components of the metal matrix 210 can depend on the desired density and load bearing properties, and will generally be selectable based on common knowledge to one of skill in the art. For example, an application requiring stainless metal can include chromium present at greater than or equal to 11%, by weight, of the total weight. In one disclosed Example, the metal matrix consists of iron, carbon, and manganese present at 99.08%, 0.17%, and 0.75%, respectively, by weight of the metal matrix. It will be understood that the term "weight" as used here is interchangeable with the term "mass".

In some implementations, the term "continuous", as used in the phrase, "continuous metal matrix 210" can mean that the metal matrix is formed as, or is present as, a unitary, integral body. In such implementations, and as a negative example, a structure formed of two distinct metal bodies held together such as with an adhesive or with a weld would be discontinuous. In some implementations, the term "continuous" as used herein can mean that a continuous metal matrix 210 is substantially compositionally and structurally homogeneous throughout its occupied volume. For simplicity, the continuous metal matrix 210 will be alternatively referred to herein as "metal matrix 210", i.e. the word "continuous" will at times be omitted without changing the meaning.

In some implementations of the CF-MMC 200, the at least one reinforcing carbon fiber 220 can be fully encapsulated within the continuous metal matrix 210. In various implementations, the expression, "encapsulated within the continuous metal matrix 210" can mean that the at least one reinforcing carbon fiber 220 is, partially or fully: encased in, enclosed in, enveloped in, integrated into, or otherwise contactingly surrounded by, the continuous metal matrix 210. In some implementations, the expression, "encapsulated within the continuous metal matrix 210" can mean that at least a portion of individual fibers comprising the at least one reinforcing carbon fiber 220 are contactingly surrounded by the continuous metal matrix 210. In some implementations, the expression, "encapsulated within the continuous metal matrix 210" can mean that the continuous metal matrix 210 is, partially or fully: formed around or otherwise contactingly disposed around the at least one reinforcing carbon fiber 220.

In some implementations, the expression stating that the at least one reinforcing carbon fiber 220 is "encapsulated within the metal matrix" means that the metal matrix 210 is formed around and within the reinforcing carbon fiber 220 with sufficiently high contact between surfaces of the metal matrix 210 and surfaces of the reinforcing carbon fiber 220 to hold the reinforcing carbon fiber 220 in place relative to the metal matrix 210. In some implementations, the expression stating that the reinforcing carbon fiber 220 is "encapsulated within the metal matrix" means that an interacting surface of the metal matrix 210 is presented to and bonded with all sides of individual polymer fibers that constitute the reinforcing carbon fiber 220.

In various implementations, the expression, "sufficiently high contact between surfaces of the metal matrix and surfaces of the reinforcing carbon fiber to hold the reinforcing carbon fiber in place relative to the metal matrix can mean that at least 50%, or at least 60%, or at least 70% or at least 80%, or at least 90% of the surface area of the reinforcing carbon fiber 220 is contacted by the metal matrix.

In general, the CF-MMC 200 will have a total density that is less than the density of pure metal. For example, mild metal such as AISI grades 1005 through 1025 has a density of about 7.88 g/cm$^3$. In contrast, an exemplary CF-MMC 200 of the present disclosure has a density of 4.8 g/cm$^3$, about 61% of the density of mild metal. In comparison to this, recently developed metal-aluminum alloys have a density approximately 87% that of mild metal.

Figure 4:
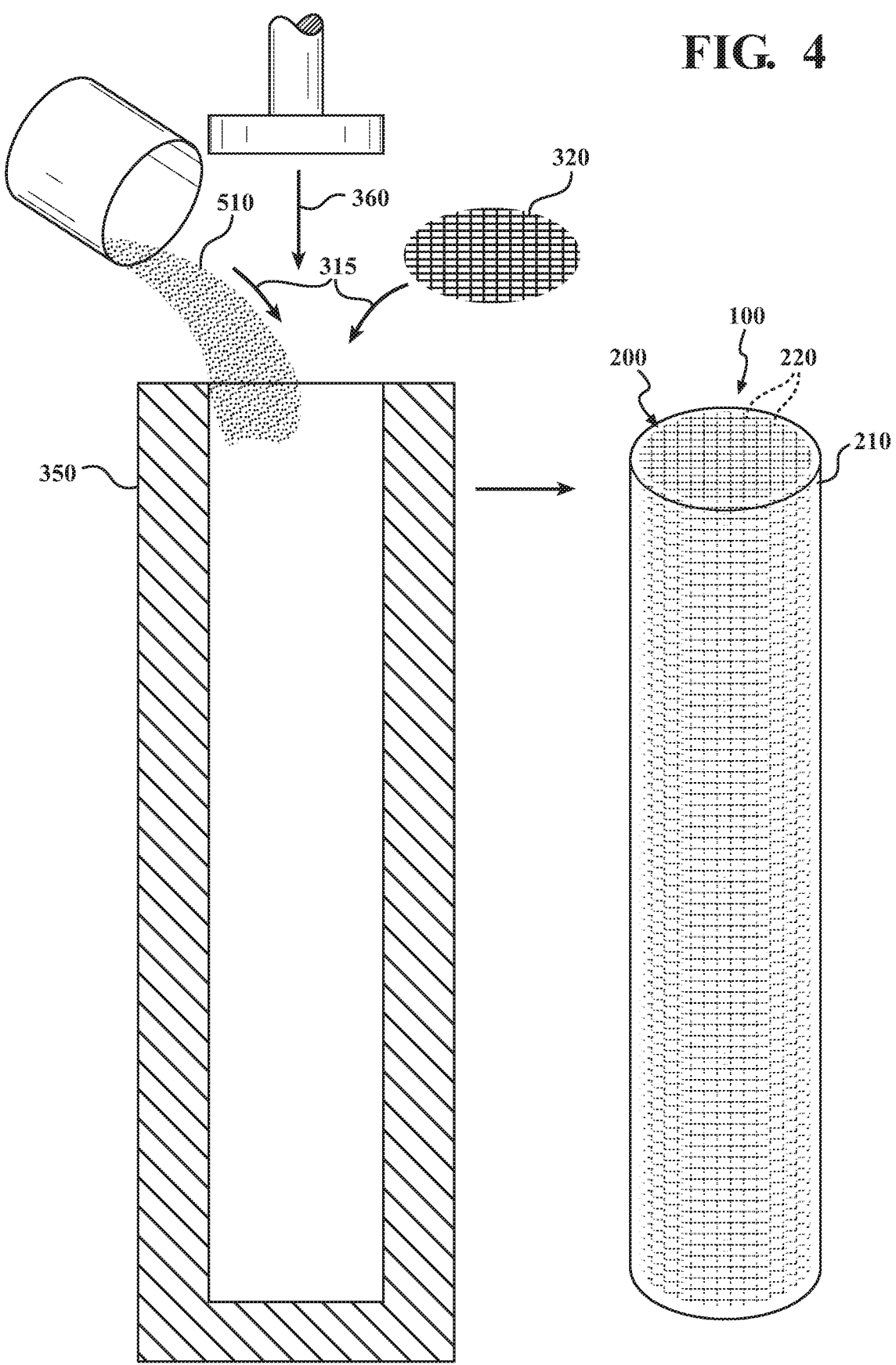
FIG. 4 is an exemplary schematic illustration of the forming of a carbon fiber metal matrix material, shown having multiple layers of reinforcing carbon fiber positioned perpendicular to a longitudinal axis of the structure.

While FIG. 4 illustrates a CF-MMC 200 having multiple layers of reinforcing carbon fiber 220 positioned perpendicular to a longitudinal axis of the structure, it is to be understood that the composite material can include randomly distributed reinforcing carbon fiber 220, reinforcing carbon fiber 220 layers positioned in a different orientation, or any other arrangement. The at least one reinforcing carbon fiber 220 can, in some implementations, include a plurality of mutually contacting or spatially separated layers of reinforcing carbon fiber. It is further to be understood that the weight ratio of reinforcing carbon fiber 220 to metal matrix 210 within the CF-MMC 200 can be substantially varied, and that such variation will have a direct influence on the density of the CF-MMC 200 given the considerably different densities of various polymers, such as aromatic polyamides (about 2.1 g/cm$^3$), and metal.

Thus, in some implementations, a CF-MMC 200 of the present disclosure will have density less than 7 g/cm$^3$. In some implementations, a CF-MMC 200 of the present disclosure will have density less than 6 g/cm$^3$. In some implementations, a CF-MMC 200 of the present disclosure will have density less than 5 g/cm$^3$.

Also disclosed is a method for forming a CF-MMC 200. With reference to FIG. 2, the method includes a step of providing metal nanoparticles 310. The term "metal nanoparticles 310" refers generally to a sample consisting predominantly of particles of metal having an average maximum dimension less than 100 nm. Individual particles of the metal nanoparticles 310 will generally consist of any alloy as compositionally described above with respect to the metal matrix 210 of the CF-MMC 200. For example, if the continuous metal matrix 210 will be formed of stainless steel, individual particles of the metal nanoparticles 310 will generally include iron and carbon; and can optionally include any, several, or all, of: manganese, nickel, chromium, molybdenum, boron, titanium, vanadium, tungsten, cobalt, niobium, phosphorus, sulfur, and silicon.

As described above with respect to the metal matrix 210 of a CF-MMC 200, relative ratios of the various elemental components of the metal nanoparticles 310 can depend on the desired application, and will generally be selectable based on common knowledge to one of skill in the art. In a disclosed Example, the individual particles of the metal nanoparticles 310 consist of iron, carbon, and manganese present at 99.08%, 0.17%, and 0.75%, respectively, by weight.

In various aspects, the average maximum dimension of the metal nanoparticles 310 can be determined by any suitable method, including but not limited to, x-ray diffraction (XRD), Transmission Electron Microscopy, Scanning Electron Microscopy, Atomic Force Microscopy, Photon Correlation Spectroscopy, Nanoparticle Surface Area Monitoring, Condensation Particle Counter, Differential Mobility Analysis, Scanning Mobility Particle Sizing, Nanoparticle Tracking Analysis, Aerosol Time of Flight Mass Spectroscopy, or Aerosol Particle Mass Analysis.

In some implementations, the average maximum dimension will be an average by mass, and in some implementations will be an average by population. In some instances, the metal nanoparticles 310 can have an average maximum dimension less than about 50 nm, or less than about 40 nm, or less than about 30 nm, or less than about 20 nm, or less than about 10 nm.

In some aspects, the average maximum dimension can have a relative standard deviation. In some such aspects, the relative standard deviation can be less than 0.1, and the metal nanoparticles 310 can thus be considered monodisperse.

With continued reference to FIG. 4, the method for forming CF-MMC 200 additionally includes a step of combining 315 the metal nanoparticles 310 with a reinforcing carbon fiber component 320 to produce an unannealed combination. The reinforcing carbon fiber component 320 is in all respects identical to the reinforcing carbon fiber 220 as described above with respect to a CF-MMC 200, with the exception that the reinforcing carbon fiber component 320 is not yet integrated into, or encapsulated within, a metal matrix 210 as defined above. Thus, the reinforcing carbon fiber component 320 can include, for example, carbon fibers formed in any configuration designed to impart tensile strength in at least one dimension, in some aspects in at least two-dimensions.

In many implementations, the combining step 215 will include sequentially combining at least one layer of metal nanoparticles 310 and at least one layer of reinforcing carbon fiber component 320, such that the unannealed combination consists of one or more layers each of metal nanoparticles 310 and reinforcing carbon fiber component 320. Any number of layers of metal nanoparticles 310 and any number of layers of reinforcing carbon fiber component 320 can be employed. It will be understood that in implementations where reinforcing carbon fiber 220 is desired at an exterior surface of the CF-MMC 200, a reinforcing carbon fiber component 320 will be the first and/or last sequentially layered component in the unannealed combination; and in implementations were reinforcing carbon fiber 220 is desired between exterior surfaces of the CF-MMC 200, a layer of reinforcing carbon fiber component 320 will be preceded and followed by a layer of metal nanoparticles 310.

The combining step 215 will generally include combining the metal nanoparticles 310 and the reinforcing carbon fiber component 320 within a die, cast, mold, or other shaped structure having a void space corresponding to the desired shape of the CF-MMC 200 to be formed. In some particular implementations, the at least one layer of metal nanoparticles 310 and the at least one layer of reinforcing carbon fiber component 320 will be combined within a heat press die 350.

In some implementations, the method for forming CF-MMC 200 can include a step of manipulating metal nanoparticles 310 in the unannealed combination into interstices in the reinforcing carbon fiber component 320. Such a manipulating step can be effective to maximize surface area of contact between metal nanoparticles 310 and the reinforcing carbon fiber component 320 in the unannealed combination, improving the effectiveness of integration of the reinforcing carbon fiber 220 into the metal matrix 210 of the eventually formed CF-MMC 200. Manipulating metal nanoparticles 310 into interstices in the reinforcing carbon fiber component 320 can be accomplished by any procedure effective to increase surface area of contact between metal nanoparticles 310 and reinforcing carbon fiber component 320, including without limitation: pressing, agitating, shaking, vibrating, sonicating, or any other suitable procedure.

The method for forming CF-MMC 200 additionally includes a step of sintering the metal nanoparticles 310, converting the metal nanoparticles 310 into a metal matrix 210 such that the reinforcing carbon fiber component 320 becomes reinforcing carbon fiber 220 integrated into the metal matrix 210; and thus converting the unannealed combination into CF-MMC 200. The sintering step generally includes heating the unannealed combination to a temperature less than 450° C. and sufficiently high to sinter the metal nanoparticles 310. In some implementations, the sintering step can include heating the unannealed combination to a temperature greater than 400° C. and less than 450° C. In some implementations, the sintering step can include heating the unannealed combination to a temperature greater than 420° C. and less than 450° C.

In some implementations, the sintering step can be achieved by hot compaction, i.e. by applying elevated pressure 360 simultaneous to the application of elevated temperature. In some implementations employing hot compaction, the elevated pressure can be at least 30 MPa; and in some implementations, the elevated pressure can be at least 60 MPa. Depending on the sintering conditions of temperature and pressure, the duration of the sintering step can vary. In some implementations, the sintering step can be performed for a duration within a range of 2-10 hours, and in one disclosed Example is performed for a duration of 4 hours.

The carbon fiber reinforced metal matrix composite (CF-MMC) is made by charging a die with alternating layers of metal powder and carbon fiber cloth. The metal powder used can be nanoparticles, <45 micron powder, or a mixture of the two size regimes. The weave of the carbon fiber cloth is loose enough to allow penetration between the fibers so that the metal matrix around the reinforcement is allowed to be continuous after consolidation.

The carbon fiber cloth and metal powder are assembled in the die under an inert atmosphere (inside an argon glove box) to prevent oxidized surfaces from forming. The final punch and die assembly is then compacted at 800° C. with 60 MPa of pressure for 1 hour, under an argon flow.

The carbon fiber has a lower density than metal (by a factor of ~3.75) and has a higher tensile strength. Addition of multiple carbon fiber layers to the metal matrix lowers the weight of the final composite (as a function of the lower carbon fiber density) and increases the tensile strength as a function of its contribution to the mechanical strength of the composite.

It will be appreciated that in some instances, providing metal nanoparticles 310 having a desired composition, average maximum dimension, and/or relative standard deviation of the average maximum dimension may be difficult to achieve by conventional methods. For example, "top down" approaches involving fragmentation of bulk metal into particulate metal via milling, arc detonation, or other known procedures will often provide metal particles that are too large and/or too heterogeneous for effective sintering into a uniform, robust metal matrix 210. "Bottom up" approaches, such as those involving chemical reduction of dissolved cations, will often be unsuitable for various alloy nanoparticles due to incompatible solubilities, or even unavailability, of the relevant cations. For example, cationic carbon, that is suitable for chemical co-reduction with cationic iron to form metal, may be difficult to obtain. Further, even where these techniques or others may be effective to produce metal nanoparticles 310 of a given composition at laboratory scale, scale up may prove unfeasible or uneconomical.

For these reasons, the step of providing metal nanoparticles 310 can in many implementations be performed by a novel metal nanoparticle 310 synthesis using Anionic Element Reagent Complexes (AERCs). An AERC generally is a reagent consisting of one or more elements in complex with a hydride molecule, and having a formula:

$$Q^0 \cdot X_y \qquad \text{Formula I,}$$

wherein $Q^0$ represents a combination of one or more metal elements, each formally in oxidation state zero and not necessarily in equimolar ratio relative to one another; X represents a hydride molecule, and y is an integral or fractional value greater than zero. An AERC of Formula I can be formed by ball-milling a mixture that includes: (i) powders of each of the one or more elements, present at the desired molar ratios; and (ii) a powder of the hydride molecule, present at a molar ratio relative to the combined one or more elements that corresponds to y. In many implementations, the hydride molecule will be a borohydride, and in some specific implementations the hydride molecule will be lithium borohydride.

Contacting an AERC of Formula I with a suitable solvent and/or ligand molecule will result in formation of nanoparticles consisting essentially of the one or more elements, the one or more elements being present in the nanoparticles at ratios equivalent to which they are present in the AERC.

Thus, an AERC suitable for use in metal nanoparticle 310 synthesis generally has a formula:

$$Fe_aC_bM_dX_y \quad \text{Formula II,}$$

where Fe is elemental iron, formally in oxidation state zero; C is elemental carbon, formally in oxidation state zero; M represents one or more elements in oxidation state zero, each of the one or more elements selected from a group including Mn, Ni, Cr, Mo, B, Ti, V, W, Co, Nb, P, S, and Si; X is a hydride molecule as defined with respect to Formula I; a is a fractional or integral value greater than zero; b is a fractional or integral value greater than zero; d is a fractional or integral value greater than or equal to zero; and y is a fractional or integral value greater than or equal to zero. It will be appreciated that the values of a, b, and c will generally correspond to the molar ratios of the various components in the desired composition of metal. It is further to be understand that M and d are shown as singular values for simplicity only, and can correspond to multiple elements present at non-equimolar quantities relative to one another. An AERC of Formula II can alternatively be referred to as a metal-AERC.

Formation of a metal-AERC can be accomplished by ball-milling a mixture that includes: (I) a powder of a hydride molecule, such as lithium borohydride; and (II) a pre-metal mixture that includes (i) iron powder; (ii) carbon powder; and (iii) optionally, powder(s) of one or more elements selected from a group including Mn, Ni, Cr, Mo, B, Ti, V, W, Co, Nb, P, S, and Si. This mixture is to include iron powder, carbon powder, and optional powder(s) of one or more selected elements, at weight ratios identical to the weight ratios of these various components in a desired metal product. For example, in order to synthesis a stainless metal type 316 product having, by weight, 12% Ni, 17% Cr, 2.5% Mo, 1% Si, 2% Mn, 0.08% C, 0.045% P, and 0.03 S, the pre-metal mixture, to be combined with powder of a hydride molecule for ball milling, should include powders of each of these elements present in the listed percentages by weight.

Thus, in some implementations, a disclosed process for synthesizing metal nanoparticles includes a step of contacting a metal-AERC, such as one defined by Formulae I or II, with a solvent. In some implementations, the disclosed process for synthesizing metal nanoparticles includes a step of contacting a metal-AERC, such as one defined by Formulae I or II, with a ligand. In some implementations, the disclosed process for synthesizing metal nanoparticles includes a step of contacting a metal-AERC, such as one defined by Formulae I or II, with a solvent and a ligand. Contacting a metal-AERC with a suitable solvent and/or ligand will result in formation of metal nanoparticles 310 having alloy composition dictated by the composition of the metal-AERC, and thus by the composition of the pre-metal mixture from which the metal-AERC was formed.

Non-limiting examples of suitable ligands can include nonionic, cationic, anionic, amphoteric, zwitterionic, and polymeric ligands and combinations thereof. Such ligands typically have a lipophilic moiety that is hydrocarbon based, organosilane based, or fluorocarbon based. Without implying limitation, examples of types of ligands which can be suitable include alkyl sulfates and sulfonates, petroleum and lignin sulfonates, phosphate esters, sulfosuccinate esters, carboxylates, alcohols, ethoxylated alcohols and alkylphenols, fatty acid esters, ethoxylated acids, alkanolamides, ethoxylated amines, amine oxides, nitriles, alkyl amines, quaternary ammonium salts, carboxybetaines, sulfobetaines, or polymeric ligands. In some particular implementations, a ligand can be at least one of a nitrile, an amine, and a carboxylate.

Non-limiting examples of suitable solvents can include any molecular species, or combination of molecular species, capable of interacting with the constituents of an AERC by means of non-bonding or transient-bonding interactions. In different implementations, a suitable solvent for synthesis of metal nanoparticles 310 from a metal-AERC can be a hydrocarbon or aromatic species, including but not limited to: a straight-chain, branched, or cyclic alkyl or alkoxy; or a monocyclic or multicyclic aryl or heteroaryl. In some implementations, the solvent will be a non-coordinating or sterically hindered ether. The term solvent as described can in some variations include a deuterated or tritiated form. In some implementation, a solvent can be an ether, such as THF.

The foregoing description is merely illustrative in nature and is in no way intended to limit the disclosure, its application, or uses. As used herein, the phrase at least one of A, B, and C should be construed to mean a logical (A or B or C), using a non-exclusive logical "or." It should be understood that the various steps within a method may be executed in different order without altering the principles of the present disclosure; various steps may be performed independently or at the same time unless otherwise noted. Disclosure of ranges includes disclosure of all ranges and subdivided ranges within the entire range.

The headings (such as "Background" and "Summary") and sub-headings used herein are intended only for general organization of topics within the present disclosure, and are not intended to limit the disclosure of the technology or any aspect thereof. The recitation of multiple embodiments having stated features is not intended to exclude other embodiments having additional features, or other embodiments incorporating different combinations of the stated features.

As used herein, the terms "comprise" and "include" and their variants are intended to be non-limiting, such that recitation of items in succession or a list is not to the exclusion of other like items that may also be useful in the devices and methods of this technology. Similarly, the terms "can" and "may" and their variants are intended to be non-limiting, such that recitation that an embodiment can or may comprise certain elements or features does not exclude other embodiments of the present technology that do not contain those elements or features.

The broad teachings of the present disclosure can be implemented in a variety of forms. Therefore, while this disclosure includes particular examples, the true scope of the disclosure should not be so limited since other modifications will become apparent to the skilled practitioner upon a study of the specification and the following claims. Reference herein to one aspect, or various aspects means that a particular feature, structure, or characteristic described in connection with an embodiment is included in at least one embodiment or aspect. The appearances of the phrase "in one aspect" (or variations thereof) are not necessarily referring to the same aspect or embodiment.

While particular embodiments have been described, alternatives, modifications, variations, improvements, and substantial equivalents that are or may be presently unforeseen may arise to applicants or others skilled in the art. Accordingly, the appended claims as filed and as they may be amended, are intended to embrace all such alternatives, modifications variations, improvements, and substantial equivalents.

What is claimed is:

1. An orthopedic replacement comprising:
a bone connection portion, configured to contact and adhere to bone; and
a load bearing portion, configured to bear a load and formed, at least in part, of a carbon fiber metal matrix material (CF-MMC) comprising:
a continuous metal matrix comprising at least one of steel and titanium; and
a reinforcing carbon fiber that is at least partially encapsulated within the continuous metal matrix.

2. The orthopedic replacement as recited in claim 1, wherein the at least one reinforcing carbon fiber is fully encapsulated within the metal matrix.

3. The orthopedic replacement as recited in claim 1, wherein the at least one reinforcing carbon fiber is partially encapsulated within the metal matrix.

4. The orthopedic replacement as recited in claim 1, wherein the at least one reinforcing carbon fiber comprises a plurality of spatially separated layers of reinforcing carbon fiber.

5. The orthopedic replacement as recited in claim 1, having density less than 7 g/cm$^3$.

6. The orthopedic replacement as recited in claim 1, having density less than 6 g/cm$^3$.

7. The orthopedic replacement as recited in claim 1, having density less than 5 g/cm$^3$.

8. The orthopedic replacement as recited in claim 1, wherein the continuous metal matrix comprises an alloy of iron, carbon, and at least one element selected from a group including: Mn, Ni, Cr, Mo, B, Ti, V, W, Co, Nb, P, S, and Si.

9. An orthopedic replacement comprising:
a structural core formed of a carbon fiber metal matrix composite comprising:
at least one reinforcing carbon fiber;
a continuous metal matrix, of sintered steel or titanium nanoparticles, disposed around the at least one reinforcing carbon fiber; and
a space completion material at least partially covering the structural core.

10. The orthopedic replacement as recited in claim 9, having density less than 7 g/cm$^3$.

11. The orthopedic replacement as recited in claim 9, having density less than 6 g/cm$^3$.

12. The orthopedic replacement as recited in claim 9, having density less than 5 g/cm$^3$.

13. The orthopedic replacement as recited in claim 9, wherein the continuous metal matrix comprises an alloy of iron, carbon, and at least one element selected from a group including: Mn, Ni, Cr, Mo, B, Ti, V, W, Co, Nb, P, S, and Si.

14. The orthopedic replacement as recited in claim 9, wherein the steel or titanium nanoparticles have an average maximum dimension less than about 50 nm.

* * * * *